United States Patent [19]

Hannick et al.

[11] Patent Number: 4,740,502

[45] Date of Patent: Apr. 26, 1988

[54] SEMISYNTHETIC ERYTHROMYCIN ANTIBIOTICS

[75] Inventors: Steven M. Hannick, Highland Park; Larry L. Klein, Lake Forest, both of Ill.

[73] Assignee: Abbott Laboratories, North Chicago, Ill.

[21] Appl. No.: 876,541

[22] Filed: Jun. 20, 1986

[51] Int. Cl.$^4$ .................. A61K 31/70; C07H 17/08
[52] U.S. Cl. ............................. 514/29; 536/7.2; 536/7.4
[58] Field of Search ............... 514/29; 536/7.2, 7.4

[56] References Cited

U.S. PATENT DOCUMENTS

| | | | |
|---|---|---|---|
| 4,283,527 | 8/1981 | Sciavolino | 536/7.4 |
| 4,331,803 | 5/1982 | Watanabe et al. | 536/7.2 |
| 4,349,545 | 9/1982 | Gouin d'Ambrieres et al. | 536/7.4 |
| 4,496,717 | 1/1985 | Adachi et al. | 536/7.2 |

*Primary Examiner*—J. R. Brown
*Assistant Examiner*—Elli Peselev
*Attorney, Agent, or Firm*—Martin L. Katz; Michael J. Roth

[57] ABSTRACT

Semisynthetic antibiotics with improved therapeutic properties made from erythromycin are disclosed. Certain 4"-carbamates of erythromycin, its derivatives, and their salts and esters show superior in vitro antimicrobial activity and reduced gastrointestinal stimulation compared to the parent compounds.

5 Claims, No Drawings

SEMISYNTHETIC ERYTHROMYCIN ANTIBIOTICS

TECHNICAL FIELD

This invention relates to antibiotics for use in the chemotherapy of antimicrobial infections, and more particularly to antibiotics made from erythromycin which exhibit high antimicrobial activity, reduced gastrointestinal side-effects and improved therapeutic ratios.

BACKGROUND ART

Erythromycin and common derivatives are widely used and exhibit desirable activity against a number of gram-positive pathogens. Since some pathogens are less susceptible than others to these drugs, high doses of these antibiotics are occasionally necessary in the treatment of serious or widespread infections. As with all drugs, toxic effects are sometimes observed at higher dosage levels, particularly in patients who are seriously compromised by infection and thus are most in need of treatment. Unfortunately, improvements in potency and spectrum are often accompanied by an increase in toxicity, so that later generation drugs usually represent a compromise between these competing considerations. As a result, there is a continuing search for antibiotics which are more potent against certain organisms, or, preferably, against all organisms, than those currently used. Desirably, such drugs will have an improved therapeutic ratio, which is the ratio of the effective therapeutic or prophylactic dose to the toxic dose, usually expressed in terms of the $ED_{50}/LD_{50}$ ratio.

It is an object of this invention to provide novel compounds which are derivatives of erythromycin, and which have greater in vitro and in vivo potency against certain organisms than erythromycin, reduced hepatotoxicity, and increased therapeutic ratios in comparison to erythromycin.

This and other objects of this invention will be more fully understood by reference to the following disclosure.

Biedrzycki, M., "Erythromycin Derivatives. Part VI. Carbamates of Cyclic 11,12-Carbonate of Erythromycin A", *Polish Journal of Chemistry* (*Roczniki Chemii*), 52, 315 (1978) describes the synthesis of the 4"-N-phenyl carbamate of erythromycin 11,12-cyclic carbonate.

DISCLOSURE OF THE INVENTION

This invention provides novel erythromycin-4"-carbamate compounds and pharmaceutically acceptable salts and esters thereof. In structural terms, this invention provides compounds of the formula

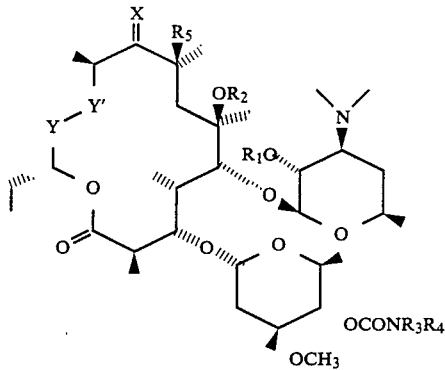

where $R_1$ is selected from hydroxyl, acyl of 2 to 20 carbon atoms, or trimethylsiloxyl, $R_2$ is hydrogen or methyl, $R_3$ and $R_4$ are independently selected from hydrogen or alkyl of 1 to 12 carbon atoms, $R_5$ is hydrogen or halogen, X is O= or $R_6ON=$ where $R_6$ is $C_1$ to $C_8$ alkyl, alkoxyalkyl, or aryl and Y—Y' is

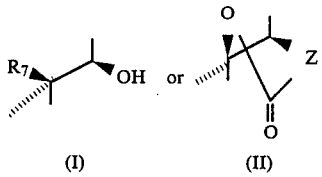

where $R_7$ is hydrogen or hydroxyl and Z is O= or $R_8N=$ where $R_8$ is hydrogen, hydroxy, alkyl, alkoxy, substituted alkyl, aryl, substituted aryl, acyl, or sulfonyl, and pharmaceutically acceptable salts thereof. Especially preferred is 2'-acetyl-erythromycin A-4"-carbamate, i.e., a compound according to the foregoing formula in which $R_1$ is acetyl, and $R_2$, $R_3$ and $R_4$ are all hydrogen, X is O=, and Y—Y' has formula (I) above in which $R_7$ is hydroxyl.

The term alkyl is used herein to mean straight, branched chain and alicyclic radicals, including, but not limited to methyl, ethyl, n-propyl, isopropyl, cyclopropyl, n-butyl, sec-butyl, isobutyl, tert-butyl, cyclohexyl and the like.

The term aryl is used herein to mean substituted and unsubstituted aromatic radicals, including, but not limited to phenyl, phenethyl, benzyl and the like.

By "substituted" alkyl or aryl is meant alkyl or aryl groups as defined above but in which one or more hydrogen atoms is replaced by a heteroatomic functional group such as amino, imino, halo, alkoxy, nitro, acetoxy, acetamido, hydroxy, cyano, and the like.

The term alkoxy is used herein to mean straight and branched chain oxygen ether radicals, including, but not limited to methoxy, ethoxy, isopropoxy, n-butoxy, sec-butoxy, isobutoxy, tert-butoxy, and the like.

The term acyl is used herein to mean straight or branched chain carbonyl radicals, including but not limited to, formyl, acetyl, propionyl, butyryl, isobutyryl and the like.

Surprisingly, certain compounds of this invention offer improved in vitro and in vivo antibiotic potency versus some bacterial species or strains in comparison to erythromycin. Further, these compounds provide an improved therapeutic ratio in comparison to potent erythromycin derivatives of the prior art.

Compounds of this invention have also been determined via testing in sensitive animal models to have markedly reduced levels of gastointestinal side-effects, such as increased motility, by virtue of their unique chemical structure. Such increased gastrointestinal motility is often seen in macrolide antibiotics of the prior art, and, while it is apparently a pharmacologic effect of the drugs rather than a toxic effect, this side effect makes such prior art compounds less preferred because the increased motility can manifest itself as cramping, nausea and/or vomiting.

By "pharmaceutically acceptable" is meant those salts and esters which are, within the scope of sound medical judgment, suitable for use in contact with the tissues of humans and lower animals without undue toxicity, irritation, allergic response, and the like, commensurate with a reasonable benefit/risk ratio, and effective for their intended use in the chemotherapy and prophylaxis of antimicrobial infections.

INDUSTRIAL APPLICABILITY

The compounds of the present invention can be used in the form of salts derived from inorganic or organic acids. Among the more common salts and esters of macrolide antibiotics are the acetate, estolate (lauryl sulfate salt of the propionate ester), ethyl succinate, gluceptate (glucoheptonate), lactobionate, stearate, and hydrochloride forms. Other acid salts used in the pharmaceutical arts are the following: adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, gluconate, glycerophosphate, hemisulfate, heptonate, hexanoate, hydrobromide, hydroiodide, 2-hydroxy-ethanesulfonate, lactate, maleate, mercaptosuccinate, methanesulfonate, 2-naphthalene-sulfonate, nicotinate, oxalate, pamoate, pantothenate, pectinate, persulfate, 3-phenylpropionate, picrate, pivalate, propionate, succinate, tartrate, thiocyanate, tosylate, and undecanoate. Although quaternized macrolide compounds are, in general, drastically less active than the parent compound in-vivo, basic nitrogen-containing groups can be quaternized with such agents as lower alkyl halides, such as methyl, ethyl, propyl and butyl chloride, bromides and iodides; dialkyl sulfates like dimethyl, diethyl, dibutyl, and diamyl sulfates; long chain halides such as decyl, lauryl, myristyl and stearyl chlorides, bromides and iodides; aralkyl halides like benzyl and phenethyl bromides and others. Water or oil-soluble or dispersible products are thereby obtained.

This invention also provides pharmaceutical compositions in unit dosage form, comprising an effective amount of a compound of this invention in combination with a conventional pharmaceutical carrier. As used herein, the term "pharmaceutical carrier" means a solid or liquid filler, diluent or encapsulating material. Some examples of the materials which can serve as pharmaceutical carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such peanut oil, cottonseed oil, safflower oil, sesame oil, olive oil, corn oil and soybean oil; polyols such as propylene glycol, glycerin, sobitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution, ethyl alcohol and phosphate buffer solutions, as well as other nontoxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents and preservatives can also be present in the compositions, according to the desires of the formulator. The amount of active ingredient that may be combined with the carrier materials to produce a single dosage form will vary depending upon the host treated and the particular mode of administration.

Injectable preparations such as sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's injection, U.S.P. and isotonic sodium chloride solution. In addition, sterile, fixed oils are conventionally employed as a solvent or suspending medium. For this purpose any bland fixed oil may be employed including synthetic and semisynthetic mono-, di- or triglycerides. In addition, fatty acids such as oleic acid find use in the preparation of injectables.

Suppositories for rectal administration can be prepared by mixing the drug with a suitable nonirritating excipient such as cocoa butter or a polyethylene glycol which is solid at ordinary temperatures but liquid at the rectal temperature and will therefore melt in the rectum and release the drug.

Solid dosage forms for oral administration may include capsules, tablets, pills, powders, prills and granules. In such solid dosage forms, the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric and other release-controlling coatings.

Liquid dosage forms for oral administration may include pharmaceutically acceptable emulsions, solutions, suspensions, syrups and elixirs containing inert diluents commonly used in the art, such as water. Such compositions may also comprise adjuvants, such as wetting agents, emulsifying and suspending agents, and sweetening, flavoring and perfuming agents.

This invention also provides methods of treating and preventing microbial infections caused by susceptible microorganisms in a human or lower animal host in need of such treatment, which method comprises administration to the human or lower animal host a therapeutically effective amount of a compound or composition of this invention. The compounds of the present invention may be administered orally, parenterally, by inhalation spray, rectally or topically in dosage unit formulations containing conventional nontoxic pharmaceutically acceptable carriers, adjuvants and vehicles as desired. The term parenteral as used herein includes subcutaneous, intravenous, intramuscular, intraarticular and intrathecal injection and infusion techniques.

Total daily dose of the compounds of this invention administered to a host in single or divided doses may be in amounts, for example, from 0.001 to 100 mg/kg body weight daily and more usually 0.01 to 1 mg/kg body weight daily. Dosage unit compositions may contain such amounts or submultiples thereof to make up the daily dose. It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The term "administration" of the antibiotic or composition herein includes systemic use, as by intramuscular, intravenous, intraperitoneal or subcutaneous injection and continuous intravenous infusion, and oral administration thereof, as well as topical application of the compounds and compositions to the site of infection or potential infection.

By "a therapeutically effective amount" of the antibiotic herein is meant a sufficient amount of the compound to treat or prevent susceptible bacterial or other microbial infections, at a reasonable benefit/risk ratio applicable to any medical treatment. Of course, the total daily usage of the compositions herein will be decided by the attending physician within the scope of sound medical judgment. The effective amount of the antibiotic of this invention will vary with the particular organism being treated, the severity of the infection, the duration of the treatment, the specific compound, ester or salt employed, the age and weight of the patient and like factors well known in the medical arts. In general, treatment regimens according to the present invention comprise administration to a patient in need of such treatment from about 100 milligrams to about 5,000 milligrams (preferably 500 to 2,000 milligrams) of the compound of this invention per day in multiple doses or, preferably, in a single dose of from about 250 milligrams to about 1,000 milligrams.

In general, the compounds of this invention are made by 2'-esterification of the parent erythromycin compound by reaction with a suitable acylating agent, such as acetic anhydride. Following this protection of the 2' position, the 4"-position is substituted in a two step reaction involving first, reaction with 4-(dimethylamino)pyridine (DMAP) and carbonyldiimidazole (CDI) to form a 4"-acyl imidazole intermediate, followed by ammonolysis of the intermediate to produce the 4" carbamate. Finally, the 2' position can be deprotected by methanolysis under mild conditions, if desired. In this reaction scheme, substitution of the appropriate amine for ammonia in the ammonolysis will yield the corresponding N-substituted carbamate under mild conditions. In this step, if the desired amine is a liquid, the solvent can be omitted.

The following examples illustrate the synthesis and use of the compounds and compositions of this invention, without intending to be limitative thereof.

EXAMPLE 1

6-O-methyl-erythromycin A-4"-carbamate

This compound was prepared by the following method:

1.2 mL (16 mmole) of acetic anhydride (neat) was added via syringe to a solution of 3 g of 6-O-methyl erythromycin A and 4.2 mL (30 mmol) of triethylamine in 20 mL of methylene chloride ($CH_2Cl_2$). After stirring at 25° C. for 12 hours under $N_2$, TLC analysis showed complete conversion to the 2'-acetylated form. The solvent was evaporated and the residue was purified by flash chromatography on silica gel with a solvent of 5% methanol in methylene chloride with 2% ammonium hydroxide. The reaction provided 3.13 grams of 2'-acetyl-6-O-methyl erythromycin A, a yield of 99% of theoretical.

3.74 grams of 2'-acetyl-6-O-methyl erythromycin A prepared in the foregoing manner and 1.73 grams of (DMAP) were dissolved in methylene chloride (50 mL) and stirred under $N_2$. 2.35 grams of carbonyldiimidazole (CDI) were added in several portions, which afforded a clear solution. After 12 hours, TLC analysis showed that the reaction was complete. The solvent was evaporated and the crude imidazolide was dissolved in 50 mL tetrahydrofuran (THF) for the next reaction step. The solution was cooled to $-78°$ C. with a dry ice bath and a great excess of ammonia (20 mL) was added via a dry ice condenser. Following addition of the ammonia, the dry ice bath was removed and the reaction mixture was warmed to reflux ($-33°$ C.). TLC analysis showed complete reaction after 15 minutes, and the ammonia was allowed to evaporate overnight. The residue was partitioned between ethyl acetate (EtOAc) and water, and the organic layer was separated. This layer was washed three times with 0.5M $NaH_2PO_4$, once with saturated $NaHCO_3$, and once with brine. The solution was dried over $Na_2SO_4$ and the solvents were evaporated to yield crude 2'-acetyl-6-O-methyl-erythromycin A 4"-carbamate. This was combined with methanol under nitrogen and heated to 50° C. for 26 hours, at which time TLC analysis showed complete methanolysis of the 2'-ester. The solvent was removed by evaporation and the crude solids obtained were purified by flash chromatography on silica gel using 10% methanol in methylene chloride with 2% $NH_4OH$ as before. The result was 3.44 g of 6-O-methyl-erythromycin A 4"-carbamate which was determined by HPLC to be over 95% pure, indicating a 91% overall yield from the starting compound.

300 MHz $^1HNMR$ ($CDCl_3$): 0.85 (3H, t), 1.1–1.3 (29H, m), 1.4 (3H, s), 1.4–1.95 (5H, m), 2.3 (6H, s), 2.44 (1H, d), 2.56 (1H, m), 2.85–3.1 (2H, m), 3.05 (3H, s), 3.2 (1H, dd), 3.33 (3H, s), 3.46 (1H, brs), 3.65 (1H, m), 3.67 (1H, d), 3.76 (1H, s), 3.79 (1H, d), 4.0 (1H, brs), 4.33 (1H, dq), 4.51 (1H, d), 4.54 (1H, d), 4.76 (2H, brs), 4.97 (1H, d), 5.06 (1H, dd).

Structure was also confirmed with mass spectra [$m/e$791 (M+H$^+$) 202 (4"-carbamoyl cladinose), 174 (desosamine)] and TLC.

EXAMPLE 2

Erythromycin B-4"-carbamate

This compound was prepared by the procedure used in example 1, and provided similar yields.

300 MHz $^1HNMR$ ($CDCl_3$): 0.86 (3H, t), 0.88 (3H, d), 1.0 (3H, d), 1.1–1.25 (23H, m), 1.45 (3H, s), 1.55–1.8 (6H, m), 2.0 (1H, m), 2.13 (1H, m), 2.26 (6H, s), 2.42 (1H, d), 2.55 (1H, dt), 2.77 (1H, m), 2.9–3.05 (1H, m), 3.27 (1H, dd), 3.33 (3H, s), 3.63 (1H, d), 3.65 (1H, m), 3.91 (1H, d), 4.1 (1H, d), 4.38 (1H, dq), 4.52 (1H, d), 4.54 (1H, d), 4.91 (1H, d), 5.37 (1H, dd), 5.56 (2H, brs).

Structure was also confirmed with mass spectra [$m/e$ 761 (M+H+) 202 (4″-carbamyl cladinose), 174 (desosamine)] and TLC.

EXAMPLE 3

2'-O-acetyl Erythromycin A 9-O-(2-methoxyethoxyethyl)oxime-4″-carbamate 1.00 g of erythromycin A 9-O-(2-methoxyethoxyethyl)oxime was dissolved in 11 mL of methylene chloride and treated with 0.36 mL of triethylamine and 0.19 mL of acetic anhydride at 45° C. for 10 hours. The reaction mixture was then diluted with 50 mL of methylene chloride, washed with saturated aqueous NaHCO$_3$ and brine, dried over MgSO$_4$ and concentrated to give 1.05 g of the acetyl oxime.

MS (FAB+): 880 (M+H)+.
IR (CCl$_4$): 1735, 1748 cm$^{-1}$.

The foregoing prepared material was dissolved in 10 mL of THF and treated with 0.684 g of DMAP and 0.912 g of CDI under an inert atmosphere at room temperature (RT) for 2 hours. Subsequently, the reaction mixture was diluted with 50 mL of EtOAc, washed with 10% aqueous NaH$_2$PO$_4$ and brine, and dried with MgSO$_4$. The solution was concentrated to dryness and the residue was dissolved in 15 mL of THF. 15 mL of ammonia were distilled into the solution and the ammonia was allowed to evaporate over 5 hours. The reaction mixture was then diluted with 50 mL of EtOAc, washed with 10% aqueous NaH$_2$PO$_4$ and brine, and dried with MgSO$_4$. Concentration and column chromatography on silica gel with 1% methanol/2% ammonium hydroxide/methylene chloride gave 0.51 g of the acetylcarbamyl oxime.

MS (FAB+): 922 (M+H)+.
IR (CCl$_4$): 1740, 1748 cm$^{-1}$.

0.493 g of the foregoing material was dissolved in 40 mL of methanol and the solution was stirred at 50° C. for 18 hours. The solvent was subsequently evaporated, giving 0.450 g of the carbamyl oxime.

MS (FAB+): 880 (M+H)+.
IR (CCl$_4$): 1735, 1745 cm$^{-1}$.

EXAMPLE 4

Erythromycin A-4″-carbamate 10.6 g of 2'-O-acetyl erythromycin A were dissolved in 100 mL methylene chloride and treated with 3.3 g of CDI and 5.0 g of DMAP for 18 hours at RT under exclusion of moisture. The solution was diluted with 150 mL methylene chloride, washed with 10% aqueous NaH$_2$PO$_4$ and brine, dried with MgSO$_4$, and concentrated to dryness. The residue was dissolved in 50 mL of THF. 50 mL of ammonia were distilled into the solution and the ammonia was allowed to evaporate over 5 hours. The reaction mixture was then diluted with 150 mL of EtOAc, washed with 10% aqueous NaH$_2$PO$_4$ and brine, dried with MgSO$_4$, and concentrated to dryness. Recrystallization from acetonitrile gave 5.04 g of the acetyl carbamate.

5.04 g of the foregoing material was dissolved in 50 mL of methanol and the solution was stirred at 40° C. for 60 hours. The solvent was subsequently evaporated, and the residue was recrystallized from EtOAc-hexane, giving 3.74 g of the carbamate.

MS (FAB+): 777 (M+H)+.
IR (CCl$_4$): 1740 cm$^{-1}$.

EXAMPLE 5

4″-carbamyl-Erythromycin A-11,12-cyclic carbonate 25.0 g of erythromycin A 11,12-cyclic carbonate were dissolved in 125 mL of methylene chloride and the resulting solution was treated with 13 g of potassium carbonate and 24 mL of acetic anhydride at reflux for 4 hours. The solution was diluted with 125 mL of methylene chloride, washed with saturated aqueous sodium bicarbonate and brine, dried with MgSO$_4$, and concentrated to dryness. Recrystallization from EtOAc gave 20.9 g of the acetyl carbonate.

2.52 g of the foregoing material were dissolved in 20 mL of THF and treated with 1.63 g of DMAP and 2.15 g of CDI at RT for 2 hours with the exclusion of moisture. Subsequently, the reaction mixture was diluted with 75 mL of EtOAC, wash with 10% aqueous NaH$_2$PO$_4$ and brine, and dried with MgSO$_4$. The solution was concentrated to dryness and the residue was dissolved in 20 mL of THF. 20 mL of ammonia were distilled into the solution and the ammonia was allowed to evaporate over 1 hour. The reaction mixture was then diluted with 150 mL of EtOAc, washed with 10% aqueous NaH$_2$PO$_4$ and brine, and dried with MgSO$_4$. Concentration gave the crude carbamate.

0.38 g of the foregoing compound was dissolved in 70 mL of methanol and the solution was stirred at 50° C. for 3 days. The solvent was subsequently evaporated, and the residue was chromatographed on silica gel with 1% methanol/2% ammonium hydroxide/methylene chloride to give 0.34 g of the carbamyl cyclic carbonate.

MS (DCI, NH$_3$): 803 (M+H)+.
IR (CCl$_4$): 1750, 1815 cm$^{-1}$.

EXAMPLE 6

4″-carbamyl-Erythromycin A-9-O-methyl oxime 4.00 g of erythromycin A 9-O-methyl oxime were dissolved in 50 mL of methylene chloride and treated with 1.58 mL of triethylamine and 0.83 mL of acetic anhydride for 6 hours at reflux. The reaction mixture was then diluted with 50 mL of methylene chloride, washed with saturated aqueous NaHCO$_3$ and brine, dried over MgSO$_4$ and concentrated to give 4.6 g of the crude acetyl oxime as a white solid.

MS (FAB+): 805 (M+H)+.
IR (CCl$_4$): 1740, 1748 cm$^{-1}$.

4.6 g of the foregoing material were dissolved in 45 mL of THF and treated with 3.0 g of DMAP and 4.0 g of CDI at RT for 2 hours with the exclusion of moisture. Subsequently, the reaction mixture was diluted with 125 mL of EtOAc, washed with 10% aqueous NaH$_2$PO$_4$ and brine, and dried with MgSO$_4$. The solution was concentrated to 50 mL, 50 mL of ammonia were distilled into the solution, and the ammonia was allowed to evaporate over 16 hours. The solvent was evaporated and the residue was recrystallized from methylene chloride-acetonitrile. The acetyl carbamyl oxime ether was isolated as 3.50 gram of a free-flowing white powder.

MS (FAB+): 848 (M+H)+.
IR (CCl$_4$): 1740 cm$^{-1}$.

1.00 g of the foregoing material was dissolved in 25 mL methanol and the solution was stirred for 16 hours at 50° C. The solution was evaporated to dryness and column chromatographed on silica gel with 1% methanol/2% ammonium hydroxide/methylene chloride to give 0.34 g of the carbamyl oxime.

EXAMPLE 7

4''-Carbamyl-8-fluoro erythromcin A 1.00 g 8-fluoro erythromycin A is dissolved in 11 mL of methylene chloride and treated with 0.36 mL of triethylamine and 0.19 mL of acetic anhydride for 10 hours at 45° C. The reaction mixture is then diluted with 50 mL of methylene chloride, washed with saturated aqueous $NaHCO_3$ and brine, dried over $MgSO_4$ and concentrated to give the acetate.

1.05 g of the foregoing material are dissolved in 10 mL of THF and treated with 0.68 g of DMAP and 0.912 g of CDI at RT for 2 hours under an inert atmosphere. Subsequently, the reaction mixture is diluted with 50 mL of EtOAc, washed with 10% aqueous $NaH_2PO_4$ and brine, and dried with $MgSO_4$. The solution is concentrated to dryness, and the residue is dissolved in 50 mL of THF. 15 mL of ammonia are distilled into the solution, and the ammonia is allowed to evaporate over 5 hours. The reaction mixture is diluted with 50 mL of EtOAc, washed with 10% aqueous $NaH_2PO_4$ and brine, and dried with $MgSO_4$. Concentration and column chromatography on silica gel with 1% methanol/2% ammonium hydroxide/methylene chloride yields the acetyl carbamyl macrolide.

0.50 g of the foregoing material is dissolved in 40 mL methanol and solution is stirred for 18 hours at 50° C. The solvent is evaporated, giving the carbamyl macrolide.

EXAMPLE 8

4''-carbamyl-6-O-methyl-11-deoxy-11-amino erythromycin A 11,12-cyclic carbamate Synthesis of the 11,12-cyclic carbamates of erythromycin is disclosed in the commonly assigned, prior copending application of Baker and Clark, "Semisynthetic Erythromycin Antibiotics", Filed June 4, 1986, Ser. No. 870,489, the disclosures of which are incorporated herein by reference in their entirety. The dicarbamate compounds of this invention can be made stepwise from the 11,12-cyclic carbamates in the manner of this invention to yield either symmetrical or mixed dicarbamates. Alternatively, symmetrical dicarbamates (having the same N-substituent at the 11,12- and 4''-positions) can be made by a somewhat different route, in which the reaction conditions used to make the 11,12-cyclic carbamate are also employed to form the 4''-carbamate. This latter method is illustrated by the following synthesis.

To a solution of 5.28 g (6.70 mmol) of 2'-acetyl-6-O-methyl erythromycin A in 125 mL of THF at −50° C. were added 10 mL (1.5 equiv) of 1M sodium hexamethyldisilazide [$NaN_2(TMS)_2$, also called sodium bis-trimethylsilyl amide] in THF. The resulting solution was stirred for 15 minutes at −50° C., and then 5.0 g of CDI in 30 mL of dimethyl formamide were added. The resulting tan suspension was stirred for 30 minutes at −50° C. and then at RT for 1 hour. The reaction mixture was diluted with 700 mL of EtOAc, washed with 10% aqueous $NaH_2PO_4$ and brine, and dried by azeotropic concentration with benzene to yield the desired 4''-, 12-diacylimidazole-10,11-en-9-one as an amber syrup.

The crude diacylimidazole enone was dissolved in 150 mL of THF and treated with 100 ml of liquid ammonia at −33° C. The ammonia was permitted to evaporate overnight at RT. The reaction mixture was then diluted with EtOAc and washed with 10% aqueous $NaH_2PO_4$ and brine. Drying with $MgSO_4$ and concentration gave the expected dicarbamyl enone.

The crude dicarbamyl enone was dissolved in 200 mL of dry THF and treated with 100 mg of potassium t-butoxide at 0° C. for 20 minutes. Dilution with EtOAc, washing with aqueous $NaH_2PO_4$ and brine, drying with $MgSO_4$ and concentration gave the expected 4''-carbamyl-11,12-cyclic carbamate.

All of the crude material from the previous step was heated in 75 mL of methanol at 50° C. for 18 hours to remove the 2'-acetyl group. Concentration and column chromatography ($SiO_2$, 1% MeOH/2% $NH_4OH/CH_2Cl_2$) gave 3.5 g of the desired macrolide, which was then recrystallized from EtOAc/hexanes to give 2.05 g of the desired 4''-carbamyl-6-O-methyl-11-deoxy-11-amino erythromycin A 11,12-cyclic carbamate as a free flowing white powder.

MS (DCI, $NH_3$): 816 (M+H)+.
IR ($CCl_4$): 1700 (w), 1748, 1780 (b) cm$^{-1}$.
NMR ($CDCl_3$): 5.80 ppm (s, 1H).

EXAMPLE 9

The compounds of this invention have been tested for gastrointestinal stimulating activity in a dog model at 4 mg/kg intravenously. Contractions in the gut were recorded with surgically implanted strain gauges. The contractile scores were determined according to the method of Jacoby, et al., as described in "Gastrointestinal Actions of Metoclopramide," *Gastroenterology*, Vol. 52, No. 4 (1967), pp. 676–684 by giving a numerical score to the height of each recorded contraction in the one hour period after administration of the test compound. A gastrointestinal motility index was expressed as the ratio of the contractility score for the test compound to the score for erythromycin A lactobionate. Ratios were calculated for the stomach, duodenum and jejunum, and a final arithmetic mean index was calculated and reported in Table I.

TABLE 1

| Substituent | Gastrointestinal Motility Index | | |
|---|---|---|---|
| | Ery A | Ery B | 6-O—Me—Ery A |
| None | 1.45 | 2.47 | 0.37 |
| 4''-carbamate | 0.11 | 0.17 | 0.03 |

Administration of erythromycin A and B lactobionates at 4 mg/kg intravenously resulted in pronounced stimulation of the stomach, duodenum, jejunum and ileum. The figure for erythromycin A, the internal standard, is greater than 1 because the stimulation actually increases with repeated doses. Administration of the 4''-carbamates of these compounds at 4 mg/kg intravenously resulted in negligble apparent stimulation of the gastrointestinal tissues. 6-O-methyl erythromycin A evoked less of a gastrointestinal response, but even with this compound the 4''-carbamate produced substantially less motility. This illustrates that the compounds of this invention are devoid of or have significantly less gastrointestinal stimulation than the parent compounds at this dosage level.

EXAMPLE 10

The antimicrobial spectrum of the 6-O-methyl-erythromycin A 4''-carbamate of this invention was tested by the following method:

Twelve petri dishes containing successive aqueous dilutions of the test compound mixed with 10 ml of sterilized Brain Heart Infusion agar (Difco 0418-01-5) are prepared. Each plate is inoculated with 1:100 (or 1:10 for Slow-growing strains, primarily Micrococcus and Streptococcus) dilutions of up to 32 different microorganisms, using a Steers replicator block. The inoculated plates are incubated at 35°-37° C. for 20-24 hours. In addition, a control plate, using BHI agar containing no test compound, is prepared and incubated at the beginning and end of each test.

An additional plate containing a compound having known susceptibility patterns for the organisms being tested and belonging to the same antibiotic class as the test compound is also prepared and incubated as a further control, as well as to provide test-to-test comparability. Erythromycin A was used for this purpose.

After incubation, each disk is read. The MIC is defined as the lowest concentration of drug yielding no growth, a slight haze, or sparsely isolated colonies on the inoculum spot as compared to the growth control.

The results are indicated in the following table.

TABLE 2

| Organism | MIC (ug/ml) | MIC-Std. |
|---|---|---|
| Staph. aureus ATCC 6538P | .02 | .2 |
| Staph. aureus CMX 686B | .05 | .2 |
| Staph. aureus A5177 | .39 | .39 |
| Staph. aureus 45 | .02 | .1 |
| Staph. aureus 45 RAR 2 | .05 | .2 |
| Staph. epidermidis 3519 | .05 | .1 |
| Staph. epidermidis 3519 RARI | .1 | .2 |
| Micrococcus luteus 9341 | .02 | .02 |
| Micrococcus luteus 4698 | .39 | .2 |
| Strep. faecium ATCC 8043 | .05 | .05 |
| Strep. bovis A5169 | .02 | .02 |
| Strep. agalactiae CMX 508 | .02 | .02 |
| Strep. pyogenes EES61 | .01 | .01 |
| Strep. pyogenes 930 | >100 | >100 |
| E. coli JUHL | 12.5 | 25 |
| E. coli SS | .2 | .2 |
| E. coli DC-2 | 50 | 50 |
| E. coli H560 | 6.2 | 6.2 |
| E. coli KNK 437 | 25 | 50 |
| Ent. aerogenes ATCC 10348 | 25 | 50 |
| Klebsiella pneumoniae 8045 | 50 | 25 |
| Providencia stuartii CMX 640 | 100 | >100 |
| Pseudomonas aeruginosa BMH10 | 50 | 100 |
| Pseudomonas aeruginosa 5007 | 50 | >100 |
| Pseudomonas aeruginosa K799/WT | 50 | 50 |
| Pseudomonas aeruginosa K799/61 | 1.56 | 1.56 |
| Pseudomonas cepacia 2961 | 50 | 100 |
| Acinetobacter SP CMX 669 | 6.2 | 3.1 |

These microbial inhibition results illustrate the efficacy of the compounds of this invention for both prevention and treatment of infections by susceptible microorganisms, including bacteria, mycoplasmae, and other pathogens.

What is claimed is:

1. A compound of the formula

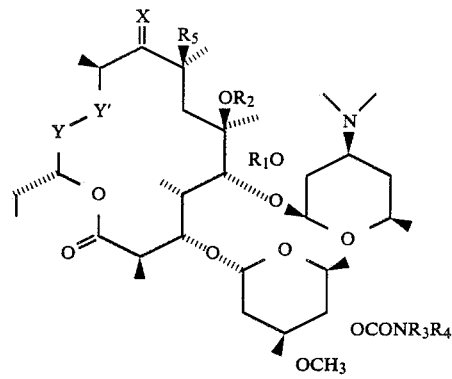

wherein $R_1$ is selected from hydroxyl or acyl of 2 to 20 carbon atoms, $R_2$ is hydrogen or methyl, $R_3$ and $R_4$ are independently selected from hydrogen or alkyl of 1 to 12 carbon atoms, $R_5$ is hydrogen or halogen, X is O= or $R_6N$= where $R_6$ is $C_1$ to $C_8$ alkyl, alkoxyalkyl, or aryl and Y—Y' is

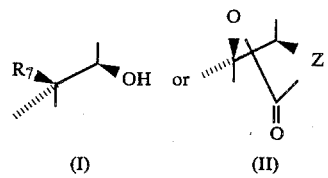

where $R_7$ is hydrogen or hydroxyl and Z is O= or $R_8N$= where $R_8$ is hydrogen, hydroxy, alkyl, substituted alkyl, alkoxy, aryl, or substituted aryl, and pharmaceutically acceptable salts thereof.

2. A compound according to claim 1 wherein $R_1$ is acetyl.

3. A compound according to claim 2 wherein $R_2$, $R_3$ and $R_4$ are all hydrogen, X is O=, and Y—Y' has the formula

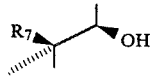

wherein $R_7$ is hydroxyl.

4. A pharmaceutical composition in unit dosage form, comprising a compound according to claim 1 in an amount effective to treat an infection caused by susceptible microorganisms in combination with a pharmaceutical carrier.

5. A method of treating infections caused by susceptible microorganisms in humans and lower animals in need of such treatment, comprising administering to the human or lower animal a therapeutically effective amount of a composition according to claim 4.

* * * * *